United States Patent
Pruthi et al.

(10) Patent No.: US 6,264,982 B1
(45) Date of Patent: Jul. 24, 2001

(54) DIETARY SUPPLEMENT COMPOSITION FOR THE TREATMENT OF HEMORRHOIDS

(76) Inventors: Som C. Pruthi; Jasvant Rai Pruthy; Puneet Pruthy, all of 25675 Meadow View Ct., Salinas, CA (US) 93908

( * ) Notice: Subject to any disclaimer, the term of this patent is extended or adjusted under 35 U.S.C. 154(b) by 0 days.

(21) Appl. No.: 09/668,239

(22) Filed: Sep. 23, 2000

Related U.S. Application Data

(63) Continuation-in-part of application No. 09/491,016, filed on Jan. 25, 2000, now abandoned.

(51) Int. Cl.[7] ............................. A61K 35/78; A61K 9/66
(52) U.S. Cl. .................... 424/455; 424/452; 424/464; 424/465; 424/761; 424/769; 424/776; 424/779
(58) Field of Search ..................... 424/452, 455, 424/464, 465, 761, 769, 776, 777

(56) References Cited

U.S. PATENT DOCUMENTS

| | | | |
|---|---|---|---|
| 5,591,436 | * 1/1997 | Pruthi ................. | 424/195.1 |
| 5,858,371 | * 1/1999 | Singh et al. ........... | 424/195.1 |

* cited by examiner

*Primary Examiner*—Herbert J. Lilling
(74) *Attorney, Agent, or Firm*—Robert M. Downey, PA

(57) ABSTRACT

A composition for a dietary supplement for use in treating hemorrhoids (bleeding and non-bleeding) includes: 30%–80% Indian Barberry extract by weight; 15%–67% Karchi seeds by weight; 2%–9% Margosa tree leaves by weight; and 1%–10% Soap Nut fruit shells by weight.

6 Claims, No Drawings

DIETARY SUPPLEMENT COMPOSITION FOR THE TREATMENT OF HEMORRHOIDS

This is a continuation-in-part of patent application Ser. No. 09/491,016 filed on Jan. 25, 2000 now abandoned.

BACKGROUND OF THE INVENTION

1. Field of the Invention

The present invention relates to an ayurvedic composition, and more particularly, to a composition comprised of natural ingredients for the treatment of hemorrhoidal symptoms including bleeding, itching, burning, swelling and pain.

2. Description of the Related Art

Presently, there are millions of people around the world who suffer from hemorrhoids. A common condition, characterized by a mass of dilated tortuous veins in swollen tissue situated at the anal margin, hemorrhoids can be a source of extreme discomfort and pain to both men and women. Depending on the severity of the condition, there are various treatments and medical procedures which presently used to alleviate the pain or to remove hemorrhoidal veins and swollen tissue. People suffering from minor hemorrhoids are ordinarily advised to use laxatives or stool softeners to reduce pain. Additionally, less severe cases are typically treated with topical ointments, such as petroleum jelly based products, to lubricate and, in some instances, numb the inflamed hemorrhoidal mass. In more severe cases, it may be necessary to reduce pain and inflammation by injection of cortisteriod drugs or other medicinal drugs having the effect of reducing swelling and pain. Otherwise, banding may be required in order to push the hemorrhoids back into the rectal cavity. All of these treatment methods are generally useful to reduce the pain and discomfort of hemorrhoids. However, all of these treatment methods set forth above provide only temporary relief and must be repeated during and throughout flare-ups of the hemorrhoidal condition.

The most severe cases of hemorrhoids often require cryosurgery or a hemorrhoidectomy to surgically remove the hemorrhoids. These procedures, while generally effective, are painful and considerably expensive. For this reason, surgical removal of hemorrhoids is a last resort performed only on those patients having severe, chronic hemorrhoidal flare-ups.

Both the present composition and my previous composition disclosed in U.S. Pat. No. 5,591,436 address the need for a less expensive, yet effective means of treating hemorrhoids without side effects and without toxicity. The present invention, as disclosed and claimed herein, improves upon my previous composition. In particular, the present invention provides a composition of natural ingredients for the long term treatment of hemorrhoids, including severe cases.

SUMMARY OF THE INVENTION

The present invention is directed to a composition for the long term treatment of hemorrhoidal symptoms including: bleeding; itching; burning; swelling; and pain.

In a preferred embodiment, the composition is comprised of natural ingredients and is manufactured in a powder form. The final product, incorporating the composition, may be in the form of capsules, tablets, syrup or in a liquid form for oral consumption or subcutaneous injection. Specifically, the dietary supplement of the present invention includes four ingredients, namely Indian Barberry extract taken from boiled Indian Barberry plant parts, Karchi seeds, Margosa tree leaves, and Soap Nut fruit shells.

Indian Barberry is known botanically as Berberis Aristata, extract taken from Indian Barberry plant parts, is present in the amount of between 30%–80% by weight of the composition. Karchi, a small tropical tree, is known botanically as Holarrhena Antidysentrica. Powder from ground Karchi seeds is present in the composition in an amount of between 15%–67% by weight of the composition. Soap Nut is known botanically as Sapindus Trifoliatus. Powder from ground Soap Nut fruit shells is present in an amount of between 1%–10% by weight of the composition. Finally, Margosa tree leaves, are known botanically as Azadirachta Indica. Powder produced by grinding the Margosa tree leaves is present in an amount of between 2%–9% by weight of the composition.

In a preferred embodiment, the dietary supplement composition of the present invention is provided capsules in an amount of between 450 milligrams to 1350 milligrams per capsule.

With the foregoing in mind, it is a primary object of the present invention to provide a dietary supplement for alleviating the symptoms associated with hemorrhoids including bleeding, itching, swelling, and pain.

It is another object of the present invention to provide a dietary supplement for treating the symptoms of both bleeding and non-bleeding hemorrhoids.

It is a further object of the present invention to provide a dietary supplement for treating the symptoms of severe cases of hemorrhoids.

It is still a further object of the present invention to provide a dietary supplement for treating the symptoms of hemorrhoids, wherein the dietary supplement consists of a composition of all natural ingredients.

It is still a further object of the present invention to provide a dietary supplement, comprising all natural ingredients, which provides a long term treatment of the symptoms of hemorrhoids without side effects.

It is still a further object of the present invention to provide a dietary supplement, comprising all natural ingredients, which provides long term treatment of the symptoms of hemorrhoids without toxicity.

It is still a further object of the present invention to provide a dietary supplement which is effective in alleviating the symptoms associated with hemorrhoids and which is inexpensive and fast acting with no side effects.

These and other objects and advantages of the present invention will be more readily apparent in the description which follows.

DETAILED DESCRIPTION OF THE PREFERRED EMBODIMENT

The fundamental elements of the composition of the present invention include Indian Barberry extract in an amount of between 30%–80% by weight of the composition; Karchi seeds in an amount of between 15%–67% by weight of the composition; Margosa tree leaves in an amount of between 2%–9% by weight of the composition; and Soap Nut fruit shells in an amount of between 1%–10% by weight of the composition.

Indian Barberry is a fruit (berries) which grows on the Indian Barberry plant known by the botanical name Berberis Aristata. Karchi is a small tropical tree and is known by the botanical name Holarrhena Antidysentrica. Margosa tree leaves are taken by the Margosa tree which is known by the botanical name Azadirachta Indica. Soap Nut fruit shell is taken from the fruit which grows on the Soap nut tree. The Soap Nut tree is a large tree that grows in clusters and is known by the botanical name Sapindus Trifolatus.

The composition of the present invention is prepared by first grinding the dried Karchi seeds, the dried Soap Nut fruit shells, and the dried Margosa tree leaves to form powders. Specifically, dried Karchi seeds are ground in a series of steps, using a series of sieves to separate smaller particles from larger particles between grinding steps. It is preferable to use a mortar and pestle to grind the particles in each step of separation, until a fine powder is produced. To prevent loss of the healing properties of this natural herb, it is important to avoid excessive heating during the grinding process of the Karchi seeds. Dried Soap Nut fruit shells are also ground in a series of steps. Again, excessive heating during the grinding process must be avoided to prevent loss of healing properties. Dried Margosa tree leaves are similarly ground to a fine powder, in a series of steps, in the same manner described above in connection with the first mixture.

Indian Barberry plant parts are broken into small pieces and then mixed with equal amounts of either water of milk in a first mixing bowl or chamber to produce a first mixture. This first mixture is heated to a boil and is maintained at a boil for 2 to 3 minutes. It is critical that this boiling time is not exceeded, as this will destroy the healing properties of the herbal ingredients. After heating, the first mixture is allowed to cool to room temperature and is then filtered to remove leaves, dirt, and other particulate to yield an extract.

All three powders of Karchi, Margosa and Soap Nut powders (as prepared above) are added to the viscous solution of Indian Barberry and thoroughly blended together to achieve a uniform blend for effective healing results and allowed to cool to a solid mass.

After drying, the blend becomes a solid mass. This solid mass is then broken into smaller pieces which are ground to produce a powder. Excessive grinding must be avoided to prevent overheating and destroying of the natural properties of the herbs. It is, therefore, best to grind the solid pieces of the blend in a series of steps, wherein smaller particles are separated from a remainder of the particles by screening. Thereafter, the smaller particles, of a predetermined maximum size, are ground separately from the larger particles in a subsequent grinding step. The larger particles are replaced in the first grinding step. This process is repeated in a series of steps to produce a fine powder. In a preferred embodiment, the process of grinding is accomplished with the use of a mortar and pestle. A series of sieves, each having a predetermined screen size (i.e., the size of the openings in the screen of the sieve), are used to separate the ground herb extract throughout the grinding process.

The powdered blend should be stored in a dry, cool place until use in the manufacturing process to produce a final product. In a preferred embodiment, the final product is provided in the form of a capsule. Each manufactured capsule, incorporating the composition of the present invention, preferably contains a concentration of between 450 milligrams to 1350 milligrams of the composition. Alternatively, the powder composition may be used in the manufacturing of tablets, a syrup, or a liquid product for subcutaneous injection or oral consumption.

To treat the symptoms of hemorrhoids, the dietary supplement should be taken in a dosage of between 450 to 1350 milligrams per day. In capsule form, this may require taking two to three capsules per day. The optimum dosage for most patients seems to be 900 milligrams per day. The capsules should be taken orally on an empty stomach, with plain yogurt or plain yogurt diluted with water.

In most cases, improvement will be observed in 5 to 6 days from the beginning of treatment. In a preferred embodiment, the complete treatment course consists of two capsules a day (900 milligrams total per day) over the course of 7 to 14 days, depending on the severity of the hemorrhoidal condition. During this treatment period, white flour, white sugar, spices, alcohol, and drugs (other than those required or prescribed by a doctor) should be avoided. A diet consisting of fruits, natural juices, water and whole wheat bread is recommended.

A typical treatment over the course of one to two weeks may provide lasting results for as long as six months in alleviating hemorrhoidal symptoms of bleeding, itching, burning, swelling and pain.

In order to verify the effectiveness of the dietary supplement of the present invention in treating the symptoms of hemorrhoids, test studies were performed on 190 patients in different age groups, all of whom had a history of hemorrhoidal problems of varying degrees. These studies were conducted under the supervision of a physician. The results of four patient studies are set forth below in the following examples:

EXAMPLE 1

Male Patient
27 years of age
Term of hemorrhoidal condition (history) 4 years
Date treatment started: Nov. 9, 1999
Date treatment stopped: Nov. 19, 1999

Hemorrhoidal Condition

|  | Before | After |
| --- | --- | --- |
| Itching | Yes | No |
| Pain | Yes | No |
| Burning | Yes | No |
| Swelling | Considerable | None |
| Bleeding | None | None |
| Any side effects: | None | |

EXAMPLE 2

Male Patient
55 years of age
Terms of hemorrhoidal condition (history): 3 years
Date treatment started: Nov. 7, 1999
Date treatment stopped: Nov. 22, 1999

Hemorrhoidal Condition

|  | Before | After |
| --- | --- | --- |
| Itching | Yes | No |
| Pain | Yes | No |
| Burning | No | No |
| Swelling | Considerable | No |
| Bleeding | No | No |
| Any side effects: | None | |

EXAMPLE 3

Female Patient
45 years of age
Term of hemorrhoidal condition: 9 months
Date treatment started: Sep. 24, 1999
Date treatment stopped: Oct. 9, 1999

EXAMPLE 3-continued

Hemorrhoidal Condition

|  | Before | After |
|---|---|---|
| Itching | No | No |
| Pain | Yes | No |
| Burning | No | No |
| Swelling | Yes | No |
| Bleeding | Yes | No |
| Any side effects: | None reported | |

EXAMPLE 4

Female Patient
34 years of age
Terms of hemorrhoidal condition: 1 year 6 months

Hemorrhoidal Condition

|  | Before | After |
|---|---|---|
| Itching | Yes | No |
| Pain | Yes | No |
| Burning | No | No |
| Swelling | Considerable | No |
| Bleeding | No | No |
| Any side effects: | None | |

While the composition of the present invention has been set forth in what is believed to be a practical and preferred embodiment, it is recognized that departures may be made within the spirit and scope of the following claims which, therefore, should not be limited except within the doctrine of equivalents.

What is claimed is:

1. A composition for a dietary supplement for use in treating the symptoms associated with hemorrhoids, comprising the following ingredients:
    extract of Indian Barberry taken from boiled Indian Barberry plant parts in an amount of between 30% and 80% by weight of the composition;
    powder of dried Karchi seeds in an amount of between 15% and 67% by weight of the composition;
    powder of dried Soap Nut fruit shells in an amount of between 1% and 10% by weight of the composition; and
    powder of Margosa tree leaves in an amount of between 2% and 9% by weight of the composition.

2. A method of producing a dietary supplement composition including extract of Indian Barberry in an amount of between 30% and 80% by weight of the composition; powder of dried Karchi seeds in an amount of between 15% and 67% by weight of the composition; powder of dried Soap Nut fruit shells in an amount of between 1% and 10% by weight of the composition; and powder of Margosa tree leaves in an amount of between 2% and 9% by weight of the composition, said method comprising the steps of:

(a) breaking Indian Barberry plant parts into small pieces;
    (b) mixing the pieces of Indian Barberry plant parts with equal amounts of water or milk to produce a first mixture;
    (c) heating the first mixture to a boil and maintaining the first mixture at a boil for 2 to 3 minutes;
    (d) cooling the mixture to room temperature;
    (e) filtering the first mixture to remove non-dissolved particulate including leaves, dirt and other particulate and yielding the extract of Indian Barberry;
    (f) allowing the extract of Indian Barberry to dry into a solid mass;
    (g) breaking the solid mass of the extract of Indian Barberry into pieces and grinding the pieces, in a series of steps, to produce a powder;
    (h) grinding dried Karchi seeds, in a series of steps, to produce the powder of dried Karchi seeds;
    (i) grinding Margosa tree leaves, in a series of steps, to produce the powder of Margosa tree leaves;
    (j) grinding dried Soap Nut fruit shells, in a series of steps, to produce the powder of dried Soap Nut fruit shells; and
    (k) combining the produced powder of the extract of Indian Barberry with the produced powder of Karchi seeds, the produced powder of Margosa tree leaves, and the produced powder of dried Soap Nut fruit shells, to produce a uniform, consistent dry powder blend defining the composition.

3. A method as recited in claim 2 further comprising the step of:
    manufacturing capsules comprising said dry powder blend, wherein individual capsules contain between 450 to 1350 milligrams of the dietary supplement composition.

4. A method as recited in claim 2 further comprising the step of:
    manufacturing tablets comprising the dry powder blend, wherein individual tablets contain between 450 to 1350 milligrams of the dietary supplement composition.

5. A method as recited in claim 2 further comprising the step of:
    manufacturing a syrup comprising the dry powder blend.

6. A method as recited in claim 2 further comprising the step of:
    manufacturing a liquid for subcutaneous injection, using the dry powder blend, wherein the manufactured liquid contains the dietary supplement composition.

* * * * *